United States Patent [19]

Totani

[11] Patent Number: 4,575,550

[45] Date of Patent: Mar. 11, 1986

[54] PLATINUM COMPLEXES

[75] Inventor: Tetsushi Totani, Hyogo, Japan

[73] Assignee: Shionogi & Co., Ltd., Osaka, Japan

[21] Appl. No.: 485,584

[22] Filed: Apr. 14, 1983

Related U.S. Application Data

[63] Continuation-in-part of Ser. No. 337,514, Jan. 6, 1982, abandoned.

[30] Foreign Application Priority Data

Jan. 23, 1981 [JP] Japan .................... 56-9463

[51] Int. Cl.$^4$ ................. C07F 17/02; C07F 15/00
[52] U.S. Cl. ..................... 536/121; 556/137
[58] Field of Search ............... 260/429 R; 536/121

[56] References Cited

U.S. PATENT DOCUMENTS

| | | | |
|---|---|---|---|
| 4,200,583 | 4/1980 | Kidani et al. | 260/429 R |
| 4,203,912 | 5/1980 | Hydes et al. | 260/429 R |
| 4,225,529 | 9/1980 | Hydes et al. | 260/429 R |
| 4,234,499 | 11/1980 | Hoeschele et al. | 260/429 R |
| 4,256,652 | 3/1981 | Kidani et al. | 260/429 R |
| 4,271,085 | 6/1981 | Amundsen et al. | 260/429 R |
| 4,291,023 | 9/1981 | Hoeschele et al. | 424/180 |
| 4,322,362 | 3/1982 | Kaplan et al. | 260/429 R |

OTHER PUBLICATIONS

Johnson et al., "Cancer Treatment Reviews", 1975, vol. 2, pp. 1-6.

Primary Examiner—Johnnie R. Brown
Attorney, Agent, or Firm—Wenderoth, Lind & Ponack

[57] ABSTRACT

Platinum complexes of the following formula useful as antitumor agents with less nephro-toxicity and higher water solubility than cisplatin:

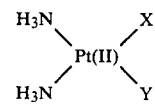

wherein X and Y respectively or taken together represent a mono- or di-valent residue of hydroxycarboxylic acids.

9 Claims, No Drawings

PLATINUM COMPLEXES

CROSS-REFERENCE TO RELATED APPLICATIONS

This application is a continuation-in-part of our prior co-pending application Ser. No. 337,514 filed Jan. 6, 1982, now abandoned.

BACKGROUND OF THE INVENTION

It has been known that various platinum compounds have antitumor activities, and for example, cisplatin (Jap. OPI 49-7224), malonato(1,2-diaminocyclohexane)-platinum (II) [Jap. OPI No. 53-31648], and sulfato(1,2-diaminocyclohexane)platinum (II) [Jap. OPI No. 54-44620] have been reported as such compounds.

The present inventors have investigated intensively to find the platinum compounds which have more potent antitumor activity and less toxicity than the prior art compounds, and have accomplished the present invention.

BRIEF SUMMARY OF THE INVENTION

The present invention relates to novel platinum complexes.

The platinum compounds in the present invention are represented by the following general formula (I).

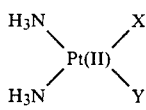

[wherein each of X and Y is a mono-valent group represented by $$-OCO-(C_mH_{2m}O_{m-1})-OH$$

or $$-OCO-(C_nH_{2n-2}O_{n-1})-OH$$

or X and Y taken together form a di-valent group represented by $$-OCO-(C_mH_{2m}O_{m-1})-O-$$

or $$-OCO-(C_nH_{2n-2}O_{n-1})-O-$$

wherein m is an integer of 1 to 6, and
n is an integer of 4 or 5)]

The compounds of the formula (I) are obtained by the reaction of cis-diamminedinitratoplatinum(II) of the formula: $Pt(NH_3)_2(NO_3)_2$ with the alkali metal salts of hydroxycarboxylic acids, and may be administered parenterally as antitumor agents.

DETAILED DESCRIPTION

In the formula (I), X and Y respectively or taken together represent a mono- or di-valent residue of hydroxycarboxylic acids. The hydroxycarboxylic acids are, e.g., glycolic acid, glyceric acid, gluconic acid, gulonic acid, glucoheptonic acid, galacturonic acid, glucuronic acid, etc., and besides naturally occurring or synthetically available hydroxycarboxylic acids applicable to the above formulae are included in the present invention.

The typical ligands represented by X and Y are shown as follows.

$$-OCOCH_2OH, -OCOCH(OH)CH_2OH,$$

$$-OCO(CHOH)_4CH_2OH, -OCO(CHOH)_5CH_2OH,$$

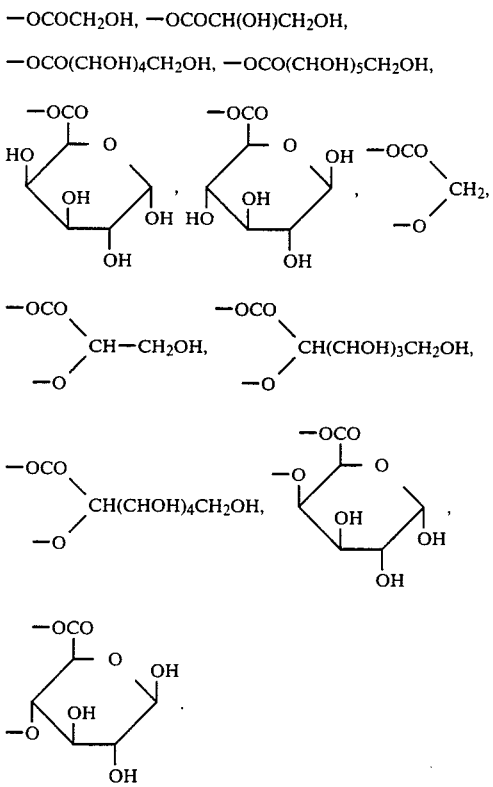

Hydroxycarboxylic acids employed in the reaction for preparing the compounds (I) are represented by the general formula:

$$HOCO-(C_mH_{2m}O_{m-1})-OH$$

or $$HOCO-(C_nH_{2n-2}O_{n-1})-OH$$

(wherein m and n have the same meanings as the above)

which may be changed into the alkali metal salts previously, if required. Hydroxycarboxylic acids are reacted with the objective alkali metal hydroxides to form the corresponding alkali metal salts. As the alkali metal salts, lithium salts, sodium salts, potassium salts, etc. may be employed, and particularly the sodium salts are preferred. For the cis-diamminedinitratoplatinum(II) an equivalent or excess amount, more preferably 1-2 equivalents of hydroxycarboxylic acids are employed in the reaction. More definitely, it is adequate to use 2 equivalents of the acids in the reaction in order to obtain the complexes in which X and Y are each a mono-valent ligand, and 1 equivalent in order to obtain the complexes in which X and Y taken together form a divalent ligand. The reaction may be carried out under heating, preferably at 50°–70° C.

The compounds in the present invention include not only those defined as ligands of the formula (I), but also all of the platinum complexes obtained by the reaction of the cis-diamminedinitratoplatinum(II) with the abovementioned hydroxycarboxylic acids within the scope of the present invention.

The compounds in the present invention have approximately the same activity as or more potent antitumor activity with less nephro-toxicity than cisplatin. Furthermore, they can easily be administered because of their high water solubility.

The compounds of the present invention can be administered to human or animals parenterally. For example, the compounds (I), dissolved or suspended in proper solvents for injection (e.g., distilled water for injection, physiological saline, 5% glucose aqueous solution, aqueous ethanol, aqueous glycerin, and aqueous propylene glycol), can be administered intravenously, intramuscularly, or subcutaneously, or by means of instillation. The compounds (I) can be placed in tightly closed ampoules as a solution or a suspension, and more preferably preserved in ampoules or vials in forms of crystals, powders, fine crystals, lyophilizate, etc., so as to be dissolved immediately before use. Stabilizer may also be added.

In application for treatment of tumors, the compounds (I) may be administered parenterally to an adult at a daily dose of 100 to 500 mg 1 to 3 times a day.

The following examples and experiments will demonstrate the present invention more in detail. The structural formulae shown in the examples are not definite, but are tentative.

EXAMPLE 1

Diglucuronato-cis-diammineplatinum(II)

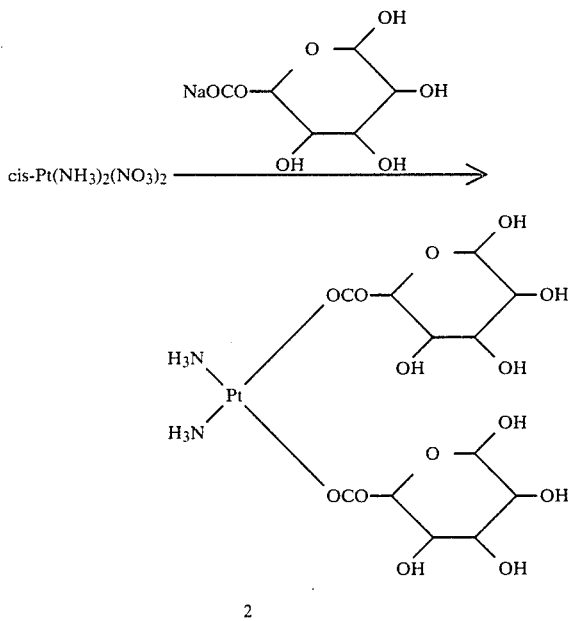

The starting compound 1 [described in Indian J. Chem. 8, 193 (1970)](700 mg, 1.98 m mole) is dissolved in water (70 ml) warmed at 60° C., and sodium D-glucuronato monohydrate (936 mg, 4 m mole) is added thereto. After stirring for a short time, water is distilled off under reduced pressure with a rotary evaporator. The residue is washed with absolute methanol (90 ml) 5 times, and then dried under reduced pressure again. This is dissolved in a small amount of water, and methanol is gradually added thereto to release viscous colored substances. The supernatant is collected by decantation and evaporated to dryness under reduced pressure. The residue is dissolved in water (5 ml) and then methanol (80 ml) is added thereto to precipitate the title compound 2 as a colorless solid. This is washed with methanol and ether successively, and dried under reduced pressure.

Yield 650 mg (54%).

mp ~150° C. (decomp.).

Elemental Analysis (for $C_{12}H_{24}O_{14}N_2Pt$). Calcd. (%): C, 23.42; H, 3.93; N, 4.55; Pt, 31.70. Found. (%): C, 22.27; H, 4.23; N, 4.74; Pt, 31.49.

IR: $\nu_{max}^{Nujol}$ ~3400 (broad, —OH), ~3270(broad, —NH), 1633 (C=O), 1400, 1285, 1151, 1047, 1020, 952, 900, 798 cm$^{-1}$.

EXAMPLE 2

Glucuronato-cis-diammineplatinum(II)

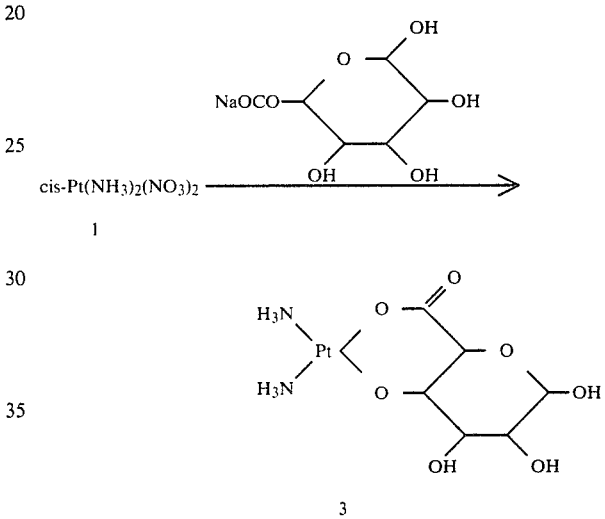

The starting compound 1 (127 mg, 0.36 m mole) is dissolved in water (12 ml) warmed at 60° C., and sodium D-glucuronate monohydrate (85 mg, 0.36 m mole) is added thereto and dissolved therein. The mixture is adjusted at pH 7 with a sodium hydroxide aqueous solution, and water is distilled off under reduced pressure at 55° C. with a rotary evaporator. The resulting colored residue is washed with absolute methanol (120 ml) and evaporated to dryness under reduced pressure again. The residue is dissolved in a small amount of water and gradual addition of methanol yields viscous colored substances. The supernatant is collected by decantation and condensed to dryness. The residue is dissolved in water (2 ml), and methanol (80 ml) is added thereto to precipitate the title compound 3 as a colorless solid. This is washed with methanol and ether successively, and then dried under reduced pressure.

Yield 65 mg (45%).

mp 170°–180° C. (decomp.).

Elemental Analysis (for $C_6H_{15}N_2O_7Pt$). Calcd. (%): C, 17.07; H, 3.58; N, 6.63. Found. (%): C, 16.39; H, 3.58; N, 6.15.

IR: $\nu_{max}^{Nujol}$ ~3380 (broad, —OH), ~3280 (broad, —NH), 1628, (C=O), 1406, 1148, 1105, 1046, 1015, 951, 824 cm$^{-1}$.

EXAMPLE 3

Digluconato-cis-diammineplatinum(II)

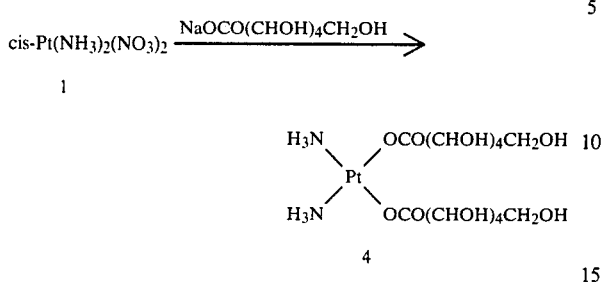

The starting compound 1 (240 mg, 0.68 m mole) is dissolved in water (24 ml) warmed at 60° C., sodium gluconate (301 mg, 1.38 m mole) is added thereto, and the mixture is stirred for a short time. The mixture is condensed to dryness at about 55° C. with a rotary evaporator. The residue is washed with absolute methanol (80 ml) and evaporated to dryness under reduced pressure again. The residue is treated in the same manner as in Example 1 to yield the title compound 4 (147 mg, yield 45%) as a colorless solid.

mp 48°–53° C. (hygroscopic and deliquescent).

Elemental Analysis (for $C_{12}H_{28}N_2O_{14}Pt$). Calcd. (%): C, 23.27; H, 4.56; N, 4.52. Found. (%): C, 22.00; H, 4.53; N, 4.91.

IR: $\nu_{max}^{Nujol}$ 3415 (broad, —OH), 3290 (broad, —NH), 1632 (C=O), 1132, 1086, 1024, 883 cm$^{-1}$.

EXAMPLE 4

Gluconato-cis-diammineplatinum(II)

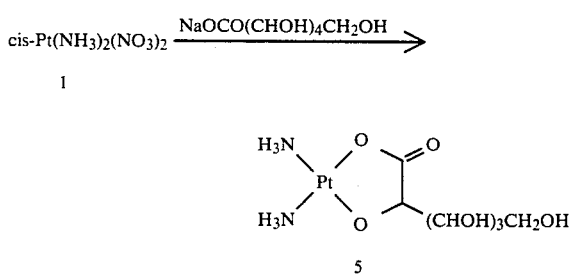

The starting compound 1 (240 mg, 0.68 m mole) is dissolved in water (24 ml) warmed at 60° C., and sodium gluconate (153 mg, 0.70 m mole) is added thereto and dissolved therein. The mixture is adjusted at pH 7 with a sodium hydroxide aqueous solution and then water is distilled off under reduced pressure at 55°–60° C. with a rotary evaporator. Then the residue is treated in the same manner as in Example 2 to yield the title compound 5 (74 mg, yield 25%) as a colorless hydrogroscopic solid.

mp ~120° C. (decomp.).

Elemental Analysis (for $C_6H_{16}N_2O_7Pt$). Calcd. (%): C, 17.03; H, 3.81; N, 6.62. Found. (%): C, 15.80; H, 3.86; N, 6.68.

IR: $\nu_{max}^{Nujol}$ ~3400 (broad, —OH), ~3280 (broad, —NH), 1632 (C=O), 1131, 1086, 1041, 866, 824 cm$^{-1}$.

EXAMPLE 5

Diglucoheptonato-cis-diammineplatinum(II)

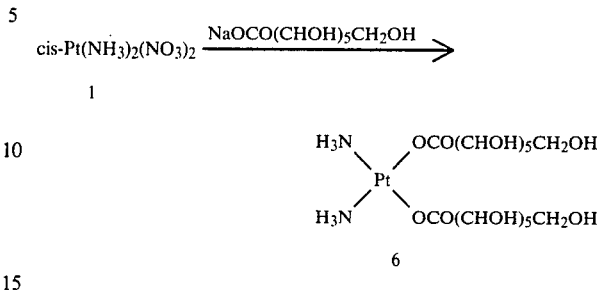

The starting compound 1 (100 mg, 0.28 m mole) is dissolved in water (10 ml) warmed at 60° C., sodium glucoheptonate dihydrate (162 mg, 0.57 m mole) is added thereto and dissolved therein. After stirring for a short time, the mixture is condensed to dryness at 55° C. with a rotary evaporator. The residue is washed with absolute methanol (80 ml) and evaporated to dryness under reduced pressure again. The residue is treated in the same manner as in Example 1 to yield the title compound 6 (75 mg, yield 39%) as a colorless hygroscopic and deliquescent solid.

mp 78°–85° C.

Elemental Analysis (for $C_{14}H_{32}N_2O_{16}Pt$). Calcd. (%): C, 24.75; H, 4.75; N, 4.12. Found. (%): C, 23.49; H, 4.79; N, 4.60.

IR: $\nu_{max}^{Nujol}$ 3230 (broad, —OH, —NH), 1620 (C=O), 1075, 1024, 884 cm$^{-1}$.

EXAMPLE 6

Glucoheptonato-cis-diamineplatinum(II)

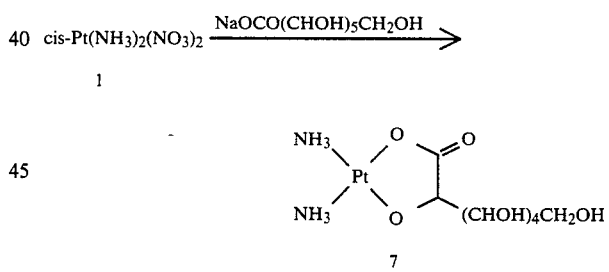

The starting compound 1 (120 mg, 0.34 m mole) is dissolved in water (12 ml) warmed at 60° C., and sodium glucoheptonate dihydrate (97 mg, 0.34 m mole) is added thereto and dissolved therein. The mixture is adjusted at pH 8 with a sodium hydroxide aqueous solution, and water is distilled off under reduced pressure at 55° C. with a rotary evaporator. The residue is washed with absolute methanol (60 ml), and evaporated to dryness again. The residue is treated in the same manner as in Example 2 to yield the title compound 7 (47 mg, 30%) as a colorless solid.

mp 155°–1602° C. (decomp.).

Elemental Analysis (for $C_7H_{18}N_2O_8Pt$). Calcd. (%): C, 18.55; H, 4.00; N, 6.18. Found. (%): C, 17.80; H, 4.24; N, 6.07.

IR: $\nu_{max}^{Nujol}$ 3425 (broad, —OH), 3285 (broad, —NH), 1612 (C=O), 1085, 1029, 844 cm$^{-1}$.

EXAMPLE 7

Glycolato-cis-diammineplatinum(II)

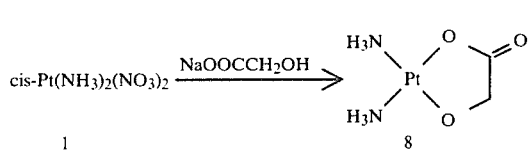

The starting compound 1 (706 mg, 2.0 m mole) is dissolved in water (30 ml) warmed at 60° C., and sodium glycolic acid (196 mg, 2.0 m mole) is added thereto and dissolved therein. The mixture is adjusted at pH 7 with a sodium hydroxide aqueous solution and stirred for 3 hours. Water is distilled off under reduced pressure at about 50° C., and the remaining solid is washed with a small amount of chilled water and dried under reduced pressure to yield the title compound 8 (92 mg, 15%).

mp 120° C.~(decomp.).

Elemental Analysis (for $C_2H_8N_2O_3Pt$). Calcd. (%): C, 7.92; H, 2.66; N, 9.24; Pt, 64.34. Found. (%): C, 7.77; H, 2.71; N, 9.34; Pt, 64.14.

IR: $\nu_{max}^{Nujol}$ 3290sh, 3210s, 1620s, 1580s, 1445m, 1330m, 1315m, 1060s, 925m, 900w, 860m, 775m $cm^{-1}$.

$^1$HNMR: ($D_2O$ solution, ppm from TMS as the external standard, δ) 4.55 (glycolato $CH_2$, $J_{195Pt-H} = 33$ Hz)

EXAMPLE 8

Glycerato-cis-diammineplatinum(II)

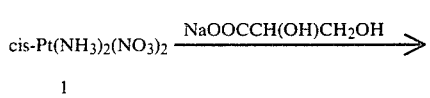

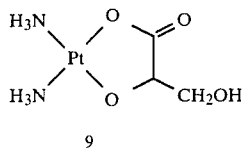

In the same manner as in Example 2 the title compound 9 is given in 45% yield.

mp 130° C.~(decomp.).

Elemental Analysis (for $C_3H_{10}N_2O_4Pt$). Calcd. (%): C, 10.81; H, 3.03; N, 8.41; Pt, 58.55. Found. (%): C, 10.99; H, 3.42; N, 8.47; Pt, 58.15.

IR: $\nu_{max}^{Nujol}$ 3400sh, 3130s, 1600s, 1560s, 1360m, 1330m, 1280w, 1225w, 1105w, 1070m, 1000m, 910w, 850w, 720m $cm^{-1}$.

$^1$HNMR: ($D_2O$ solution, ppm from TMS as the external standard, δ) 4.05–4.45 (m, glyceryl $CH_2$), 4.40–4.80 (m, glyceryl C).

EXAMPLE 9

Diglycolato-cis-diammineplatinum(II)

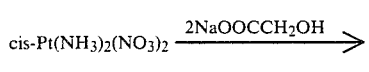

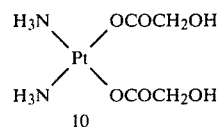

In the same manner as in Example 1 the title compound 10 is given in 79% yield.

mp 130° C.~(decomp.).

Elemental Analysis Calcd. (%): C, 12.67; H, 3.19; N, 7.39; Pt, 51.44. Found. (%): C, 12.38; H, 3.29; N, 7.43; Pt, 50.97.

IR: $\nu_{max}^{Nujol}$ 3250sh, 3200s, 1620s, 1580s, 1440m, 1330m, 1320m, 1060s, 930m, 900w, 860w, 760w, 720w $cm^{-1}$.

$^1$HNMR: ($D_2O$ solution, ppm from TMS as the external standard, δ) 4.51 (glycolato $CH_2$), 3.5–5.5 ($NH_3$).

EXAMPLE 10

Diglycerato-cis-diammineplatinum(II)

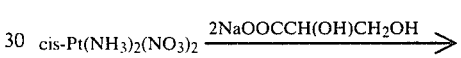

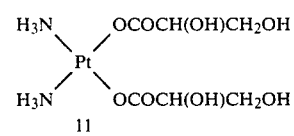

In the same manner as in Example 1 the title compound 11 is given in 86% yield.

mp 70°–80° C.

Elemental Analysis (for $C_6H_{16}N_2O_8Pt$). Calcd. (%): C, 16.40; H, 3.67; N, 6.38; Pt, 44.40. Found. (%): C, 15.73; H, 3.84; N, 6.97; Pt, 45.86.

IR: $\nu_{max}^{Nujol}$ 3350sh, 3240s, 1620s, 1110m, 1060m, 1000m, 870w, 820w, 770w, 720w $cm^{-1}$.

$^1$HNMR: ($D_2O$ solution, ppm from TMS as the external standard, δ) 4.13–4.31 (m, glycerato $CH_2$), 4.57–4.75 (m, glycerato CH), 3.80–5.40 ($NH_3$).

EXPERIMENT 1

Antitumor activity against Sarcoma-180

(Test Method)

Sarcoma 180 tumor cells ($5 \times 10^6$ cells) are inoculated to DS mice (6 to 8 mice are employed in each test group) subcutaneously, and a predetermined amount of the test compounds is administered intraperitoneally for 5 days continuously from the next day of the inoculation.

9

(Test Compound)

(A) Glucuronato-cis-diammineplatinum(II)

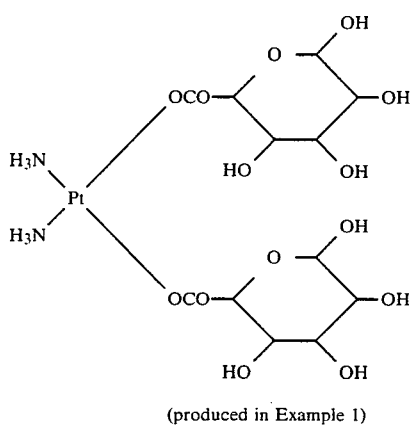

(produced in Example 1)

(B) Cisplatin (Evaluation of the Effect)

On the 10th day after the inoculation of tumors, the mice are anatomized, the weight of tumors are measured and compared with that of the untreated control group, and the effect is evaluated from the effective dose ($ED_{50}$) which inhibits the growth of tumors by 50%, the 50% lethal dose ($LD_{50}$), and the curative index (CI)*

$$*CI = \frac{LD_{50}}{ED_{50}}$$

The larger CI is, the more effective the compound is.

(Result)

(i) In the use of 5% glucose solution as a solvent for injection

| Compound | (A) | (B) |
|---|---|---|
| $ED_{50}$ | 33.4 mg/kg | 5.8 mg/kg |
| $LD_{50}$ | 93.4 mg/kg | 14.2 mg/kg |
| CI | 2.8 | 2.4 |

(ii) In the use of 0.9% NaCl, 0.4% Polysorbate 80, 0.5% CMC, and 0.5% benzyl alcohol suspension as a solvent for injection

| Compound | (A) | (B) |
|---|---|---|
| $ED_{50}$ | 34 mg/kg | 7.3 mg/kg |
| $LD_{50}$ | 113.5 mg/kg | 28.3 mg/kg |
| CI | 3.3 | 3.9 |

EXPERIMENT 2

Antitumor activity against L1210

(Test Method)

Leukemia L1210 ascites cells ($10^5$ cells) in mice are intraperitoneally inoculated to $BDF_1$ mice (4 to 10 mice are employed in each test group), and on the next day a predetermined amount of the test compounds is administered intraperitoneally. The solvent for injection consists of 0.9% NaCl, 0.4% Polysorbate 80, 0.5% CMC, and 0.5% benzyl alcohol suspension.

(Test Compound)

The same as in Experiment 1

(Evaluation of the Effect)

From the average survival days (a) in the test group and those (b) of the untreated control group, the increase of lifespan (ILS) is calculated according to the following expression.

$$ILS\ (\%) = \frac{(a) - (b)}{(b)} \times 100$$

(Result)

| Dose | Compound (A) | Compound (B) |
|---|---|---|
| 0 × 1 | | |
| 2 × 1 | 4 (%) | 11 (%) |
| 5 × 1 | 12 | 29 |
| 10 × 1 | 14 | >84 |
| 20 × 1 | >55 | −26 |

EXPERIMENT 3

Nephro-toxicity (Test Method)

Seven weeks-old male Sprague Dawley rats are separately accommodated in metabolic cages of stainless steel, and solid feed (Clea Japan, INC., CA-1 for breeding) and water are given so that they can take them freely. They are adapted for 3 days and then the test compounds are once administered to rats intraperitoneally at 10:00 a.m. The test compounds are dissolved in 5% glucose injection solution to give a 10 mg/7.5 ml solution immediately before use, and administered at a rate of 0.75 ml/100 g body weight. The urine excreted during a period of 10 a.m. on the day of administration to 10 a.m. on the next day is defined as urine of the first day; on the urine of the 0-4th days the volume of urine excreted, creatinine, osmotic pressure, urinary enzyme N-acetyl-$\beta$-D-glucosaminidase (NAG), and lysozyme (LEZ) are measured, and further urinary protein and urinary sugar are examined with Labstix ®. In the morning on the 5th day the rats are anatomized under anesthesia with Ouropan-Soda ®(Shionogi & Co., Ltd.; Hexobarbital sodium), and the blood and pathologic specimens of the kidney and the liver are collected in order to determine the level of plasma urea nitrogen and creatinine, and osmotic pressure.

(Test Compound)

The same as in Experiment 1

(Result)

| Item of Observation | Test Compound (A) | Test Compound (B) |
|---|---|---|
| Dose (Once, i.p.) | 10 mg/kg | 5 mg/kg |
| Solvent for Injection | *1 | 1  2* |
| Body Weight (g) | ± | ↓  ↓ |
| Volume of Urine (ml/24 hrs.) | ± | ↑ |
| Excrement of Creatinine (mg/24 hrs./100 g BW | ± | ↓  ± |
| Osmotic Pressure of Urine | ± | ↓  ↓ |

| | Test Compound | |
|---|---|---|
| Item of Observation | (A) | (B) |
| (mOsm/kg) | | |
| Excrement of Solute | ± | ↓ ± |
| (mOsm/24 hrs./100 g BW) | | |
| NAG | | ↑↑ ↑ |
| LEZ | ± | ↑ ↑↑ |
| Plasma Urea Nitrogen | ± | ↑ ↑ |
| Plasma Creatinine | ± | ↑ ↑ |
| Creatinine Clearance | ± | ↓ ↓ |
| Plasma Osmotic Pressure | ± | ± ± |
| Kidney Weight | ± | ↑ ↑ |
| Liver Weight | ± | ↓ ↓ |
| Urinary Protein | ± | ↑ ↑ |
| Urinary Glucose | ± | ↑ ↑ |

(Notes)
*The solvent for injection is 5% glucose in 1 and physiological saline in 2.
↑ increase
  slight increase
↓ decrease
± no change From the above results, the effect on the function of the kidney and the action on the whole body are great in cisplatin, but the presently claimed compound has little influence on them.

EXPERIMENT 4

Antitumor activity against Sarcoma-180

(Test Method)

The test was carried out in the same manner as in Experiment 1, wherein the test compounds were administered intravenously for 5 days.

(Test Compound)

(A) Glucuronato-cis-diammineplatinum(II)
(B) Cisplatin
(C) Glycolato-cis-diammineplatinum(II)

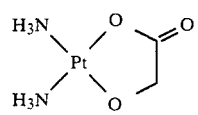

(produced in Example 7)

(D) Diglycolato-cis-diammineplatinum(II)

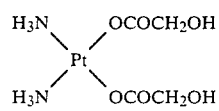

(produced in Example 9)

(E) Glycerato-cis-diammineplatinum(II)

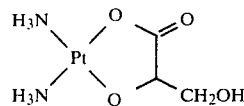

(produced in Example 8)

(Evaluation of the Effect)

The evaluation was made in the same manner as in Experiment 1.

(Result)

| Compound* | A | B | C | D | E |
|---|---|---|---|---|---|
| ED$_{50}$ (mg/kg) | 63.4 | 4.5 | 18.7 | 24.1 | 44 |
| LD$_{50}$ (mg/kg) | 186 | 14.2 | 86.6 | 80.0 | 186.6 |
| CI | 2.9 | 3.2 | 4.6 | 3.3 | 4.2 |

*Administered as 5% glucose solution.

What we claim is:

1. A platinum complex of the formula:

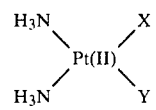

wherein each of X and Y is a mono-valent group of

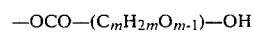

or

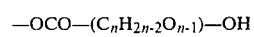

or X and Y taken together form a di-valent group of

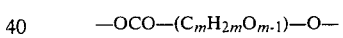

or

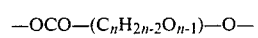

(wherein m is an integer of 1 to 6, and n is an integer of 4 to 5.)

2. A platinum complex as claimed in claim 1, wherein m is an integer of 5 or 6 and n is an integer of 5.

3. A platinum complex according to claim 1 in which the complex is diglucuronato-cis-diamineplatinum(II).

4. A platinum complex according to claim 1 in which the complex is glucuronato-cis-diamineplatinum(II).

5. A platinum complex according to claim 1 in which the complex is digulconato-cis-diamineplatinum(II).

6. A platinum complex according to claim 1 in which the complex is gluconato-cis-diamineplatinum(II).

7. A platinum complex according to claim 1 in which the complex is diglucoheptonato-cis-diamineplatinum(II).

8. A platinum complex according to claim 1 in which the complex is glucoheptonato-cis-diamineplatinum(II).

9. A platinum complex according to claim 1 in which the complex is glycolato-cis-diammineplatinum(II).

* * * * *